United States Patent
Salamon et al.

[19]
[11] Patent Number: 5,991,488
[45] Date of Patent: Nov. 23, 1999

[54] COUPLED PLASMON-WAVEGUIDE RESONANCE SPECTROSCOPIC DEVICE AND METHOD FOR MEASURING FILM PROPERTIES

[75] Inventors: Zdzislaw Salamon; Gordon Tollin; H. Angus MacLeod, all of Tucson, Ariz.

[73] Assignee: The Arizona Board of Regents on behalf of the University of Arizona, Tucson, Ariz.

[21] Appl. No.: 08/965,733

[22] Filed: Nov. 7, 1997

Related U.S. Application Data

[60] Provisional application No. 60/030,768, Nov. 8, 1996.

[51] Int. Cl.$^6$ .............................. G02B 6/12; G01B 9/02
[52] U.S. Cl. .............................. 385/129; 385/11; 385/12; 385/141; 356/346; 356/351
[58] Field of Search .............................. 385/12, 129, 131, 385/141, 11; 356/301, 300, 346, 351; 250/227.11, 227.14

[56] References Cited

U.S. PATENT DOCUMENTS

| | | | |
|---|---|---|---|
| 5,017,007 | 5/1991 | Milne et al. | 356/301 |
| 5,116,121 | 5/1992 | Knoll et al. | 356/301 |
| 5,344,784 | 9/1994 | Attridge | 436/518 |
| 5,521,702 | 5/1996 | Salamon et al. | 356/244 |
| 5,563,707 | 10/1996 | Prass et al. | 356/361 |
| 5,792,667 | 8/1998 | Florin et al. | 436/147 |
| 5,846,843 | 12/1998 | Simon | 385/131 X |

OTHER PUBLICATIONS

Salamon, Z., H.A. Macleod and G. Tollin, "Surface Plasmon Resonance Spectroscopy as a Tool for Investigating the Biochemical and Biophysical Properties of Membrane Protein Systems. I: Theoretical Principles," *Biochim. et Biophys. Acta*, 1331: 117–129 (1997).

Salamon, Z., H.A. Macleod and G. Tollin, "Surface Plasmon Resonance Spectroscopy as a Tool for Investigating the Biochemical and Biophysical Properties of Membrane Protein Systems. II: Applications to Biological Systems," *Biochim. et Biophys. Acta*, 1331: 131–152 (1997).

Salamon et al., "Surface Plasmon Resonance Spectroscopy Studies of Membrane Proteins: Transducin Binding and Activation by Rhodopsin Monitored in Thin Membrane Films," *Biophys. J.*, 71: 283–294, 1996.

Salamon, Z. and G. Tollin, "Surface Plasmon Resonance Studies of Complex Formation Between Cytochrome c and Bovine Cytochrome c Oxidase Incorporated into a Supported Planar Lipid Bilayer. I: Binding of Cytochrome c to Cardiolipin/Phosphatidylcholine Membranes in the Absence of Oxidase," *Biophvs. J.*, 11:848–857, 1996.

Salamon, Z. and G. Tollin, "Surface Plasmon Resonance Studies of Complex Formation Between Cytochrome c and Bovine Cytochrome c Oxidase Incorporated into a Supported Lipid Bilayer. II: Binding of Cytochrome c to Oxidase–Containing Cardiolipin/phosphatidylcholine Membranes," *Biophys. J.* 71:858–867, 1996.

Mueller, P., D.O. Rudin, H.T.Tien and W.C. Wescott, "Reconstitution of Cell Membrane Structure in vitro and its Transformation into an Excitable System," *Nature*, 194: 979–980, 1962.

*Primary Examiner*—Brian Healy
*Attorney, Agent, or Firm*—Antonio R. Durando

[57] ABSTRACT

A conventional SPR spectroscopic device, consisting of a metallic film used with a prism to provide a surface plasmon wave, is modified by coating the film with a dielectric layer. According to one aspect of the invention, such additional layer of dielectric material functions as an optical amplifier that produces an increased sensitivity and enhanced spectroscopic capabilities in SPR. According to another aspect of the invention, the added dielectric layer can be used as a matrix for adsorbing and immobilizing the sensing materials in sensor applications. Furthermore, the dielectric layer provides a shield for both mechanical and chemical protection of the metal layer, thereby preventing the rapid deterioration that commonly accompanies such detectors. In its simplest embodiment, the invention includes only one dielectric layer; in other embodiments, a variety of multi-layer configurations may be implemented for different purposes with diverse dielectric materials.

20 Claims, 12 Drawing Sheets

OTHER PUBLICATIONS

Salamon, Z., J.T. Hazzard and G. Tollin, "Direct Measurement of Cyclic Current–Voltage Responses of Integral Membrane Proteins at a Self–Assembled Lipid Bilayer–Modified Electrode: Cytochrome f and Cytochrome c Oxidase," *Proc. Natl. Acad. Sci. USA,* 90: 6420–6423 (1993).

Den Engelsen, "Optical Anisotropy in Ordered Systems of Lipids," *Surf. Sci.,* 56: 272–280, 1976.

Ducharme, D., J. Max, C. Saleese and R. M. Leblanc, "Ellipsometric Study of the Physical States of Phosphatidylcholines at the Air–Water Interface," *J. Phys. Chem.,* 94: 1925–1932, 1990.

COUPLED PLASMON-WAVEGUIDE RESONANCE SPECTROSCOPIC DEVICE AND METHOD FOR MEASURING FILM PROPERTIES

RELATED APPLICATIONS

This application is based on Provisional Application Ser. No. 60/030,768, pending, filed by the same inventors on Nov. 8, 1996.

U.S. GOVERNMENT RIGHTS

This invention was made with Federal Government support under contract number MCB-9404702 awarded by the National Science Foundation. The Government has certain rights in the invention.

BACKGROUND OF THE INVENTION

1. Field of the Invention

This invention pertains in general to the field of surface plasmon resonance (SPR) spectroscopy. In particular, the invention relates to a novel SPR approach involving the coupling of plasmon resonances in a thin metal film and the waveguide modes in a dielectric overcoating.

2. Description of the Related Art

Surface plasmon resonance is a technique used in the development of gas sensors, measurement of optical properties of metals, degradation monitoring of metals, microscopy, and chemical and biochemical sensing. Among optical techniques such as ellipsometry, multiple internal reflection spectroscopy, and differential reflectivity, SPR is one of the most sensitive techniques to surface and interface effects. This inherent property makes SPR well suited for nondestructive studies of surfaces, interfaces, and very thin layers. SPR also has uses other than surface investigations and it has recently been demonstrated as a new optical technique for use in immunoassays.

The SPR phenomenon has been known for over 25 years and the theory is fairly well developed. Simply stated, a surface plasmon is an oscillation of free electrons that propagates along the surface of a conductor. The phenomenon of surface plasmon resonance occurs under total internal reflection conditions at the boundary between substances of different refractive indices, such as glass and water solutions. When an incident light beam is reflected internally within the first medium, its electromagnetic field produces an evanescent wave that crosses a short distance (in the order of nanometers) beyond the interface with the second medium. If a thin metal film is inserted at the interface between the two media, surface plasmon resonance occurs when the free electron clouds in the metal layer (the plasmons) absorb energy from the evanescent wave and cause a measurable drop in the intensity of the reflected light at a particular angle of incidence that depends on the refractive index of the second medium.

Typically, the conductor used for SPR spectrometry is a thin film of metal such as silver or gold; however, surface plasmons have also been excited on semiconductors. The conventional method of exciting surface plasmons is to couple the transverse-magnetic (TM) polarized energy contained in an evanescent field to the plasmon mode on a metal film. The amount of coupling, and thus the intensity of the plasmon, is determined by the incident angle of the light beam and is directly affected by the refractive indices of the materials on both sides of the metal film. By including the sample material to be measured as a layer on one side of the metallic film, changes in the refractive index of the sample material can be monitored by measuring changes in the surface plasmon coupling efficiency in the evanescent field. When changes occur in the refractive index of the sample material, the propagation of the evanescent wave and the angle of incidence producing resonance are affected. Therefore, by monitoring the angle of incidence at a given wavelength and identifying changes in the angle that causes resonance, corresponding changes in the refractive index and related properties of the material can be readily detected.

As those skilled in the field readily understand, total reflection can only occur above a particular critical incidence angle if the refractive index of the incident medium (a prism or grating) is greater than that of the emerging medium. In practice, total reflection is observed only for incidence angles within a range narrower than from the critical angle to 90 degrees because of the physical limitations inherent with the testing apparatus. Similarly, for systems operating with variable wavelengths and a given incidence angle, total reflection is also observed only for a corresponding range of wavelengths. This range of incidence angles (or wavelengths) is referred to as the "observable range" for the purpose of this disclosure. Moreover, a metal film with a very small refractive index (as small as possible) and a very large extinction coefficient (as large as possible) is required to support plasmon resonance. Accordingly, gold and silver are appropriate materials for the thin metal films used in SPR; in addition, they are very desirable because of their mechanical and chemical resistance.

Thus, once materials are selected for the prism, metal film and emerging medium that satisfy the described conditions for total reflection and plasmon resonance, the reflection of a monochromatic incident beam is a function of its angle of incidence and of the metal's refractive index, extinction coefficient, and thickness. The thickness of the film is therefore selected such that it produces observable plasmon resonance when the monochromatic light is incident at an angle within the observable range.

The classical device by which SPR is carried out is known as the Kretschmann prism arrangement, illustrated by the sensor apparatus 10 of FIG. 1. A thin film 12 of metal is coated on one face 14 of a prism 16 which has a high refractive index n (in the 1.4–1.7 range). Gold or silver films are most often used due to their refractive and extinction properties, as described above, and the relative ease with which these metals can be deposited onto a substrate with an accurate thickness. The surface chemistry of gold and its resistance to oxidation make it the prime choice for SPR experiments, although many other materials can support surface plasmon (SP) waves. As well understood by those skilled in the art, the main criterion for a material to support SP waves is that it have a negative real dielectric component, which results from the refractive and extinction properties outlined above. Although materials other than metals can support SPR, metals are most commonly used; accordingly, metals are used here to denote a support surface for SP waves.

It is noted that another type of sensor used for conventional SPR is the Otto device, which consists of the same elements illustrated in FIG. 1 but with a very thin air gap between the face 14 of the prism 10 and the metal film 12. The principles for the design and operation of these two devices are the same. Therefore, this entire disclosure is intended to refer to both types of device even though the figures illustrate only Kretschmann prism arrangements.

The surface 18 of the metal film 12 forms the transduction mechanism for the sensor 10 and is brought into contact with the sample material 20 to be sensed at the interface between the metal film and the emerging medium contained in a cell assembly 22. Monochromatic light L is emitted by a laser or equivalent light source 24 into the prism or grating 16 and reflected off the metal film 12 to an optical photodetector 26 to create the sensor output. The light L launched into the prism and coupled into the SP mode on the film 12 is p-polarized with respect to the metal surface where the reflection takes place. According to these prior-art devices and techniques, only p-polarized light is coupled into the plasmon mode because this particular polarization has the electric field vector oscillating normal to the plane that contains the metal film. This is sometimes referred to as transverse-magnetic (TM) polarization.

As mentioned, the surface plasmon is affected by changes in the dielectric value of the material in contact with the metal film. As this value changes, the conditions necessary to couple light into the plasmon mode also change. For the particular sensing system described in FIG. 1 (and for the corresponding Otto configuration), the angle of incidence $\alpha$ for the light beam L with respect to the metal surface 18 and the reflected light intensity are the measured parameters of interest. If the angle of incidence for the light beam is scanned throughout a range of values, a distinct minimum in reflectivity is observed at a discrete angle associated with a given refractive index in the sample material 20. This angle is commonly known as $\alpha_{sp}$, the surface plasmon coupling angle. At this particular angle of incidence, set of dielectric values, and optical wavelength, the light L is being coupled into the plasmon mode and the reflection is attenuated. There is a distinct coupling angle where most of the light is attenuated for each sample material. Thus, as illustrated schematically in FIG. 2, measurements are carried out by mounting the sensor device 10 on a table 28 capable of rotating with respect to the fixed light source 24 and by relating $\alpha_{sp}$ to changes in the dielectric values or refractive index of the sample material 20.

SPR is a highly sensitive technique useful for investigating changes that occur at the surface 18 of the metal film. Therefore, the basic SPR sensor device 10 has been used in a wide variety of SPR research applications. In particular, over the last decade there has been a renewed interest in the application of surface plasmon resonance spectroscopy to study the optical properties of molecules immobilized at an interface between solid and liquid phases. This invention was made and is disclosed herein in this context. As described in detail in recently published articles, the ability of the SPR phenomenon to provide information on the physical properties of thin films deposited on a metal layer, including lipid and protein molecules forming proteolipid membranes, is based upon two principal characteristics of the effect. The first is the fact that the evanescent electromagnetic field generated by the free electron oscillations decays exponentially with penetration distance into an emergent dielectric medium; i.e., the depth of penetration into the dielectric material in contact with a metal layer extends only to a fraction of the light wavelength used to generate the plasmons. This makes the phenomenon sensitive to the optical properties of the metal/dielectric interface without any interference from the properties of the bulk volume of the dielectric material or any medium that is in contact with it. The second characteristic is the fact that the angular (or wavelength) position and shape of the resonance curve is very sensitive to the optical properties of both the metal film and the emergent dielectric medium adjacent to the metal surface. As a consequence of these characteristics, SPR is ideally suited for studying both structural and mass changes of thin dielectric films, including lipid membranes, lipid membrane-protein interactions, and interactions between integral membrane proteins and peripheral, water-soluble proteins. See Salamon, Z., H. A. Macleod and G. Tollin, "Surface Plasmon Resonance Spectroscopy as a Tool for Investigating the Biochemical and Biophysical Properties of Membrane Protein Systems. I: Theoretical Principles," *Biochim. et Biophys. Acta*, 1331: 117–129 (1997); and Salamon, Z., H. A. Macleod and G. Tollin, "Surface Plasmon Resonance Spectroscopy as a Tool for Investigating the Biochemical and Biophysical Properties of Membrane Protein Systems. II: Applications to Biological Systems," *Biochim. et Biophys. Acta*, 1331: 131–152 (1997).

The present invention is directed at improving these prior-art sensor devices and procedures by providing new thin-film interface designs that couple surface plasmon and waveguide excitation modes. The resulting devices, referred to herein as coupled plasmon-waveguide resonators (CPWR), exhibit several new properties that constitute material advances in the art.

BRIEF SUMMARY OF THE INVENTION

One primary goal of this invention is an SPR spectroscopic tool that provides greatly enhanced spectroscopic capabilities and sensitivities over conventional SPR sensors and procedures, thereby allowing a broader spectrum of applications than has heretofore been possible.

In particular, a goal of the invention is a technique that affords increased spectral resolution and improved sensitivity in SPR spectroscopy.

Another goal is an SPR spectroscopic technique that provides the ability to measure anisotropy in both the refractive index and the extinction coefficient of a medium of interest.

Another important objective is a technique that is applicable to a wide range of materials, including lipid membranes which have either integral membrane proteins incorporated into them, or peripheral membrane proteins bound to their surface.

Another goal of the invention is a tool that is particularly suitable for obtaining information about molecular assemblies that can be immobilized at a dielectric/water interface.

Yet another objective is a tool that provides protection of the plasmon-generating metallic film against mechanical or chemical deterioration during use.

Another goal is a technique that makes it possible to achieve the objectives of the invention with an efficient, practical and economically feasible implementation.

Finally, another objective is a procedure and corresponding apparatus that are suitable for direct incorporation with existing SPR spectroscopic instruments.

Therefore, according to these and other objectives, the present invention consists of a metallic (or semiconductor) layer (or layers), typically either gold or silver, used with either a prism or a grating so as to provide a surface plasmon wave, and covered with a solid dielectric layer characterized by predetermined optical parameters. According to one aspect of the invention, such additional layer of dielectric material functions as an optical amplifier that produces an increased sensitivity and enhanced spectroscopic capabilities in SPR. According to another aspect of the invention, the added dielectric layer can be used as a matrix for adsorbing and immobilizing the sensing materials in sensor applications. Furthermore, the dielectric layer provides a shield for both mechanical and chemical protection of the metal layer, thereby preventing the rapid deterioration that commonly accompanies such detectors. In its simplest embodiment, the invention includes only one dielectric layer; in other embodiments, a variety of multi-layer configurations may be implemented for different purposes with diverse dielectric materials.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The heart of this invention lies in the recognition that the addition of a dielectric layer to the metallic layer of a conventional SPR sensor provides advantages that constitute a significant advance in the art. It is understood that the dielectric layer of the invention is in addition to and separate from the sample material or analyte with which the invention is used. The sample material at the interface with the emerging medium is often itself dielectric in nature, but its properties cannot be used to obtain the advantages of the invention without the addition of an additional dielectric layer as disclosed herein. Therefore, all references to dielectric material pertain only to the additional layer contemplated by the invention.

Figure 1:
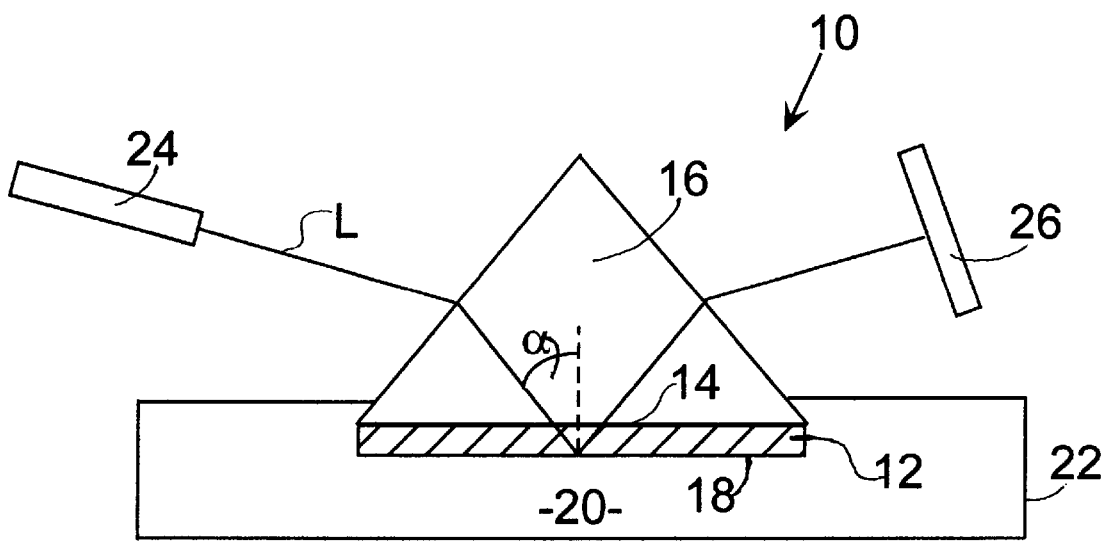
FIG. 1 is a schematic representation of a conventional Kretschmann prism arrangement for carrying out surface plasmon resonance spectroscopy.
Figure 2:
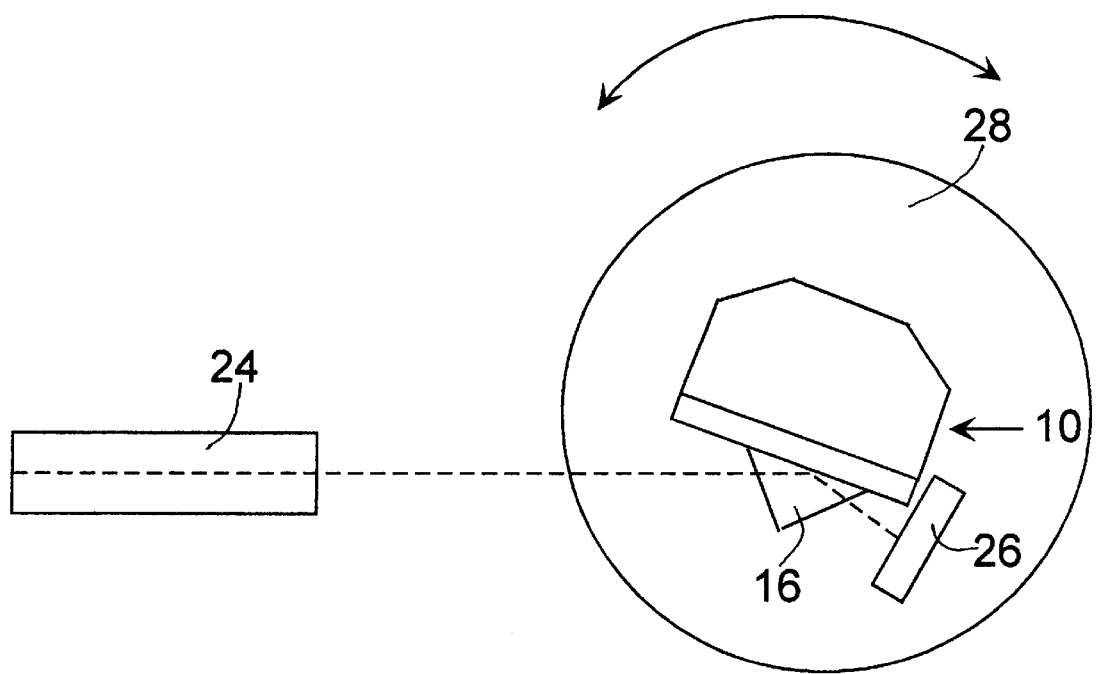
FIG. 2 is a schematic illustration of a conventional attenuated total reflection system used for SPR measurements.
Figure 3:
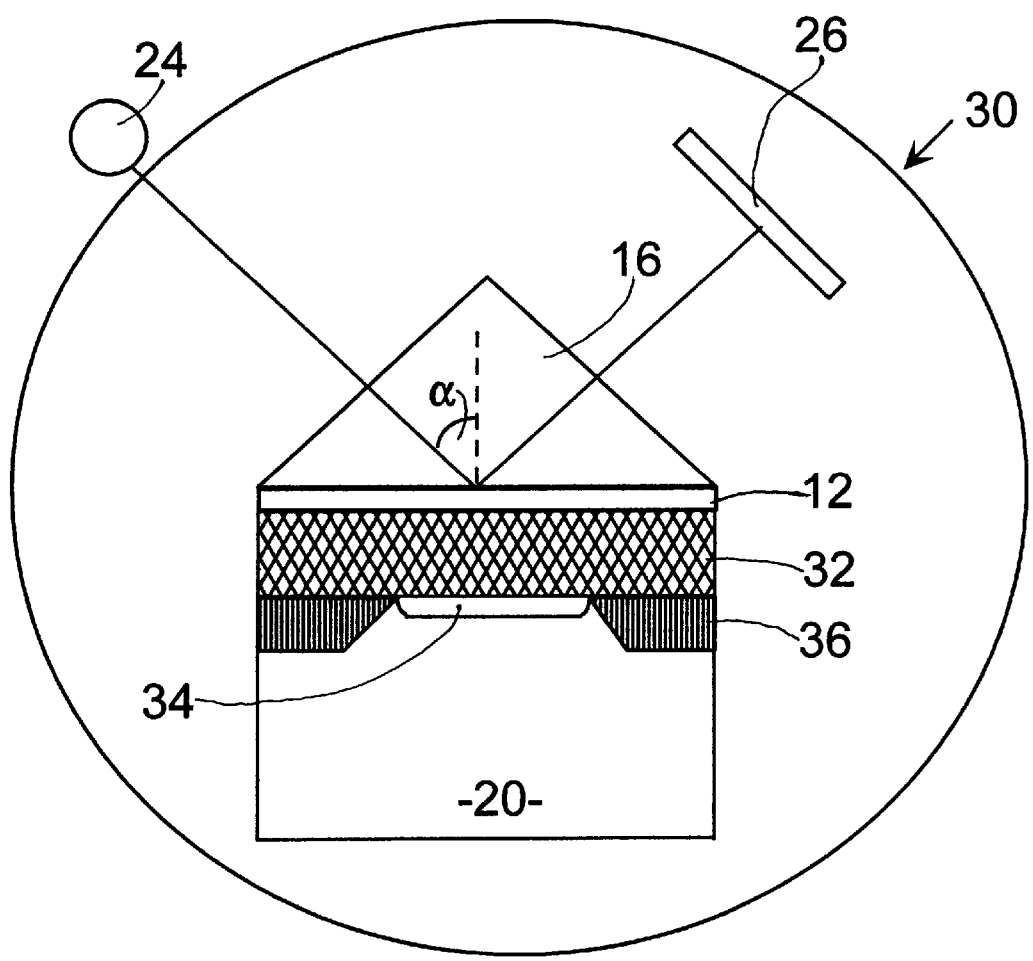
FIG. 3 is a schematic view of one embodiment of a coupled plasmon-waveguide resonance spectroscopic tool according to the invention in an attenuated total reflection measuring system, wherein a glass prism coated with a 50 nm-thick silver layer is protected by a 460 nm-thick $SiO_2$ film; a lipid bilayer is deposited on the dielectric film and held in place by a TEFLON® spacer.

Referring to the drawings, wherein like reference numerals and symbols are used for like parts, FIG. 3 illustrates in schematic form a device 30 according to one embodiment of the invention. The device 30 contains a metallic (or semiconductor) layer (or layers) 12, typically between 45 and 55 nm thick, formed from either gold or silver deposited on either a glass prism or grating 16 for generating a surface plasmon wave. (As mentioned above, the same elements could be used in an Otto configuration with an air gap between the glass and metal layer.) The silver film is covered with a layer 32 of solid dielectric material characterized by an appropriate set of values of film thickness, t, refractive index, n, and extinction coefficient, k.

Suitable dielectric materials must have a refraction index nd greater than the refractive index $n_e$ of the emerging medium; they must have an extinction coefficient $k_d$ as small as possible for a given wavelength (for example, $\leq 0.1$, preferably between 0 and 0.01, for λ=633 nm); and they must be selected with a thickness that will support a guided wave and result in the resonance effects occurring at an angle of incidence within the observable range, as defined above. For example, a glass prism coated with a 50 nm-thick silver layer protected by a 460 nm-thick $SiO_2$ film ($n_d$=1.4571, $k_d$=0.0030) is suitable to practice the invention with an aqueous analyte ($n_e$=1.33). A lipid bilayer 34 (the material being tested) is deposited from the sample solution 20 on the dielectric film 32 and held in place by a TEFLON® spacer 36 according to the teachings of U.S. Pat. No. 5,521,702 (Salamon et al.).

In the $SiO_2$ embodiment of FIG. 3, with a wavelength of about 633 nm, the dielectric material must be at least 50 nm thick to act as a waveguide. In addition, the resulting s-resonance will fall within the observable range for any thickness larger than 250 nm; on the other hand, the p-resonance will be visible for any thickness greater than 400 nm. In order to fulfill the conditions of the invention for both types of polarization, the dielectric layer must be at least 420 nm thick. Similarly, the same configuration embodied with a $TiO_2$ dielectric and a wavelength of about 633 nm would require a thickness larger than 65 nm for the s-resonance and larger than 140 nm for the p-resonance to be observable. The conditions of the invention would be met for both types of polarization with a $TiO_2$ layer at least 750 nm thick.

Figure 4:
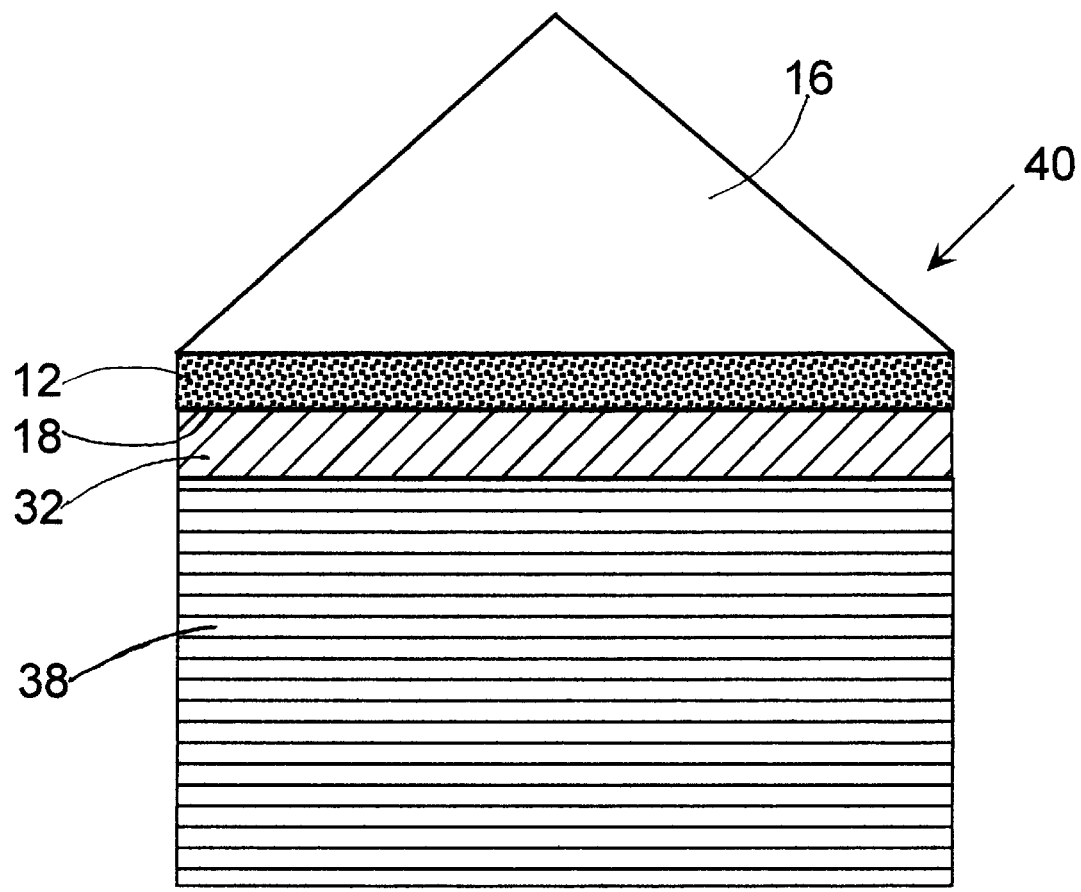
FIG. 4 is a schematic view of another embodiment of a coupled plasmon-waveguide resonance spectroscopic tool according to the invention, wherein a silver-coated glass prism contains two dielectric layers; one layer of 50 nm $TiO_2$ protects the silver film and is coated with a second 750 nm layer of a lower refractive-index dielectric material (n=1.35).

In another embodiment 40 of the invention, illustrated in FIG. 4, the silver-coated glass prism 16 includes two solid dielectric layers. One 50 nm layer 32 of $TiO_2$ ($n_d$=2.2789, $k_d$=0.000151) protects the silver film 12; a second 750 nm layer 38 of a lower density, lower refractive index (n=1.35) dielectric material ($Na_3AlF_6$) is applied over the first layer. In this example this material is selected with a lower density and a correspondingly higher porosity so as to provide a structural matrix for adsorbing and immobilizing the sensing materials 20 (hydrogels are well known materials used for this purpose).

According to one aspect of the invention, spectroscopic measurements with the devices 30 and 40 are based upon the resonant excitation of electromagnetic modes of the structure by both TM (p) and TE (s) polarized components of a continuous-wave laser light (e.g., He-Ne; λ=632.8 nm) passing through the glass prism 16 under total internal reflection conditions. We found that the addition of the dielectric layer 32, with the appropriate set of optical parameters defined above, to the conventional SPR arrangement not only provides both mechanical and chemical protection for the metal layer 12, but also produces optical amplification that results in increased sensitivity and enhanced spectroscopic capabilities.

Using the structures of FIGS. 3 and 4, it was possible to determine that the relative bandwidths of the resonances obtained with either p- or s-polarized incident light, and therefore the sensitivity of the measurement, can be varied by altering the properties of the overcoat film 32 (or films 32,38). Thus, this discovery makes it possible to both expand SPR spectroscopy to the use of s-polarized light and improve the quality of the measurements by altering the spectral response of the system. In addition, in sensor applications the added dielectric overcoat could also be used as a matrix that adsorbs and immobilizes the sensing material 20. For example, the DEXTRAN® layer that is currently used in commercial SPR biosensors for fast and efficient immobilization of ligands could be manipulated into the dielectric matrix 38 to generate resonances with widely varying sensitivities. For a detailed explanation regarding the immobilization of membrane proteins on metal or dielectric surfaces, see Salamon et al., II: Applications to Biological Systems, supra.

One way to explain the appearance of an s-polarized resonance component in a conventional SPR experiment as a consequence of adding a dielectric layer 32 onto the metal surface 18 (FIG. 4) is through the application of the electromagnetic field theory to thin-film systems (Macleod, H. A., *Thin Film Optical Filters*, Adam Hilger, Bristol, 1986). According to the theory, thin-film materials are characterized by a complex dielectric constant that includes the refractive index n and the extinction coefficient k (i.e., n−ik). In the optical region of the electromagnetic spectrum, this parameter is equal to the ratio of light velocity in vacuo (c) to that in a medium (v), and is numerically equivalent to the optical admittance, which is defined by the ratio of the amplitudes of the electric (B) and magnetic (C) fields of the electromagnetic wave, as follows:

$$Y = C/B = c/v = n - ik \qquad (1)$$

where Y is the optical admittance divided by the admittance of free space.

Using Maxwell's equations, one can describe the propagation of the plane, monochromatic, linearly polarized, and homogeneous electromagnetic field within a multilayer thin-film system with the following matrix equation:

$$\begin{bmatrix} B \\ C \end{bmatrix} = \prod_{j=1}^{s} \begin{bmatrix} \cos\beta_j & i(\sin\beta_j)/y_j \\ iy_j \sin\beta_j & \cos\beta_j \end{bmatrix} \begin{bmatrix} 1 \\ y_{j+1} \end{bmatrix} \qquad (2)$$

where s is the number of layers (32,38) deposited on the incident medium (the glass prism 16); $\beta_j = 2\pi(n_j - ik_j)t_j \cos\alpha_j/\lambda$ gives the phase thickness of layer j at the appropriate angle of incidence ($\alpha_j$) and light wavelength (λ); and $y_j = (n-ik)_j/\cos\alpha_j$ for p-polarized light and $y_j = (n-ik)_j \cos\alpha_j$ for s-polarized light.

Equation 2 and the relations governing its parameters allow examination of the distribution of electromagnetic field amplitudes throughout the thin-film system, as well as calculation of the transmittance, absorbance, and reflectance. They also allow analysis of the resonance phenomena occurring within such thin-multilayer films.

The reflectance of a multilayer system is given by the following relationship involving the optical admittance:

$$R = (y_o - Y)^2 / (y_o + Y)^2 \qquad (3)$$

where $y_o$ is the admittance of the incident medium (the glass prism 16). Based on Equation 1, the incident medium should be free from absorption, so that $y_o$ is real and equals $n_o$ at normal incidence. Equation 3 describes a reflectance spectrum, i.e., reflectance as a function of either the incident angle α using monochromatic light of predetermined wavelength λ, as used in the present description; or of varying λ at a constant value of α; or of varying the thickness of one layer at constant thickness values for the other layers and constant α and λ (an example of the latter is presented in FIGS. 5 and 6). Analysis of the optical admittance shows that beyond a critical angle for the system the emergent wave in the final medium is evanescent and the admittance is imaginary; positive imaginary for p-polarized light and negative imaginary for s-polarization. Thus, for a surface wave to be confined to the metal surface, the admittance exhibited by the adjoining medium must be positive imaginary and of magnitude very close to that of the extinction coefficient k of the metal (i.e., only materials with a small value of the refractive index n and a large value of k, such as silver and gold, will generate a surface wave). For a metallic film, this condition is fulfilled only for p-polarization and a very narrow range of angles of incidence. Coupling of the incident light to the surface wave results in the sharp dip in total internal reflectance that is characteristic of the resonance effect. For s-polarization the admittance is always negative imaginary and, therefore, there is normally no corresponding resonance. However, in the coupled plasmon-waveguide resonance device of the invention the dielectric overcoat layer 32 (or system of layers 32,38) is used to transform the admittance of the emergent medium so that the admittance presented to the metal is positive imaginary for both s- and p-polarization. Depending on the characteristics of the admittance-matching dielectric overcoat (i.e., $n_d$, $k_d$, and $t_d$ values), the system can produce a narrowing or a broadening of the range of angles over which the necessary coincidences are achieved, and hence a similar broadening or narrowing of the resonances. Examination of the distribution of electric field amplitudes through the system shows that the admittance-matching layers are important components of the resonant system, rather like cavity layers in narrowband filters or thin-film waveguides in optical couplers. The term coupled plasmon-waveguide resonance is used here in order to distinguish this resonance phenomenon from conventional surface plasmon resonance.

Since the added dielectric layer or layers of the invention make it possible to produce resonance with either s- or p-polarized light, it is desirable to select the dielectric thickness $t_d$ such that both resonance effects fall within the observable range for the system. Thus the same device can be utilized to obtain two sets of measurements from the same sample.

A large variety of dielectric overcoat film combinations (32, 38) exists that can be used in particular applications. In essence, any one layer of dielectric or combination of dielectric layers that satisfy the refractive index, extinction coefficient, and thickness requirements for producing resonance at incident angles (for a given wavelength) or at wavelengths (for a given incident angle) within the observable range is suitable for practicing the invention. For example, these materials include $MgF_2$, $Al_2O_3$, $LaF_3$, $Na_3AlF_6$, ZnS, $ZiO_2$, $Y_2O_3$, $HfO_3$, $Ta_2O_5$, ITO, and nitrites or oxy-nitrites of silicon and aluminum, which are all normally used in optical applications.

Measurements using the CPWR devices of the present invention are made in the same way as with conventional SPR techniques. As well understood in the art, the attenuated total reflection method of coupling the light into the deposited thin multilayers is used, thereby exciting resonances that result in absorption of the incident radiation as a function of either the light incident angle α (with a monochromatic light source), or light wavelength λ (at constant incident angle), with a consequent dip in the reflected light intensity.

Figure 5:
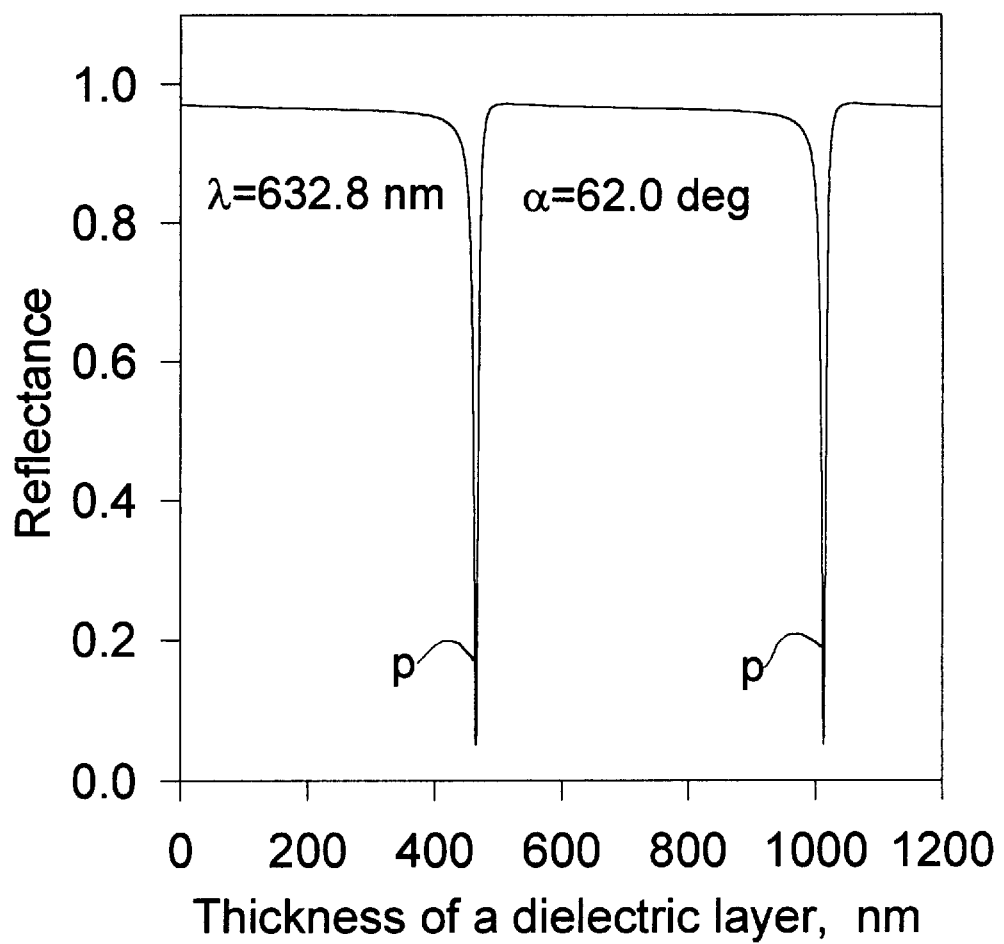
FIG. 5 shows resonance spectra presented as reflected light intensity as a function of the protective $SiO_2$ layer thickness, with p-polarized light and incident angles arbitrarily chosen in the range of usual values for SPR spectroscopy.
Figure 6:
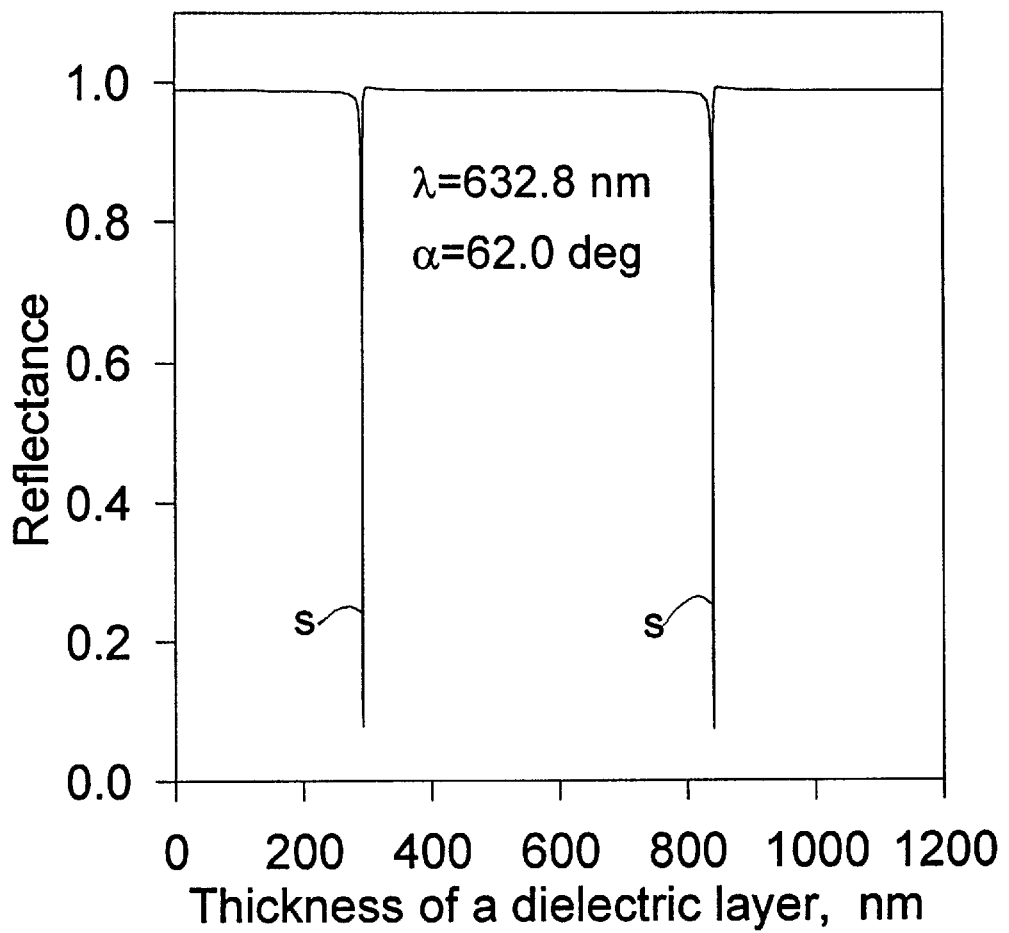
FIG. 6 shows resonance spectra presented as reflected light intensity as a function of the protective $SiO_2$ layer thickness with s-polarized light.

Thus, under appropriate experimental conditions, which are determined by the system's parameters, the devices 30 and 40 of the present invention can be excited by either p- or s-polarized light to resonantly absorb the incident light energy. FIG. 5 illustrates such resonances measured as reflected light intensity as a function of the thickness of the $SiO_2$ dielectric layer 32, obtained with p-polarized light (λ=632.8 nm) in the arrangement shown in FIG. 3 and with an incident angle α (62 degrees) arbitrarily chosen in the typical observable range for a glass-prism/aqueous-emerging-medium system (about 61 to 90 degrees). Similarly, FIG. 6 illustrates resonances measured as a function of the thickness of the $SiO_2$ layer with s-polarized light. The two resonances are separated and occur at different dielectric thicknesses, but these figures demonstrate that it is possible to adjust the thickness of the overcoat layer 32 to obtain both s- and p-resonances with the same device. The apparatus shown in FIG. 3, with a $SiO_2$ layer 32 460 nm thick applied over a 50 nm silver layer 12, and that of FIG. 4, with a combination of a 50 nm $TiO_2$ layer 32 and a 750 nm layer 38 of $Na_3AlF_6$, represent two examples of devices that exhibit the resonances shown in FIGS. 5 and 6.

Figure 7:
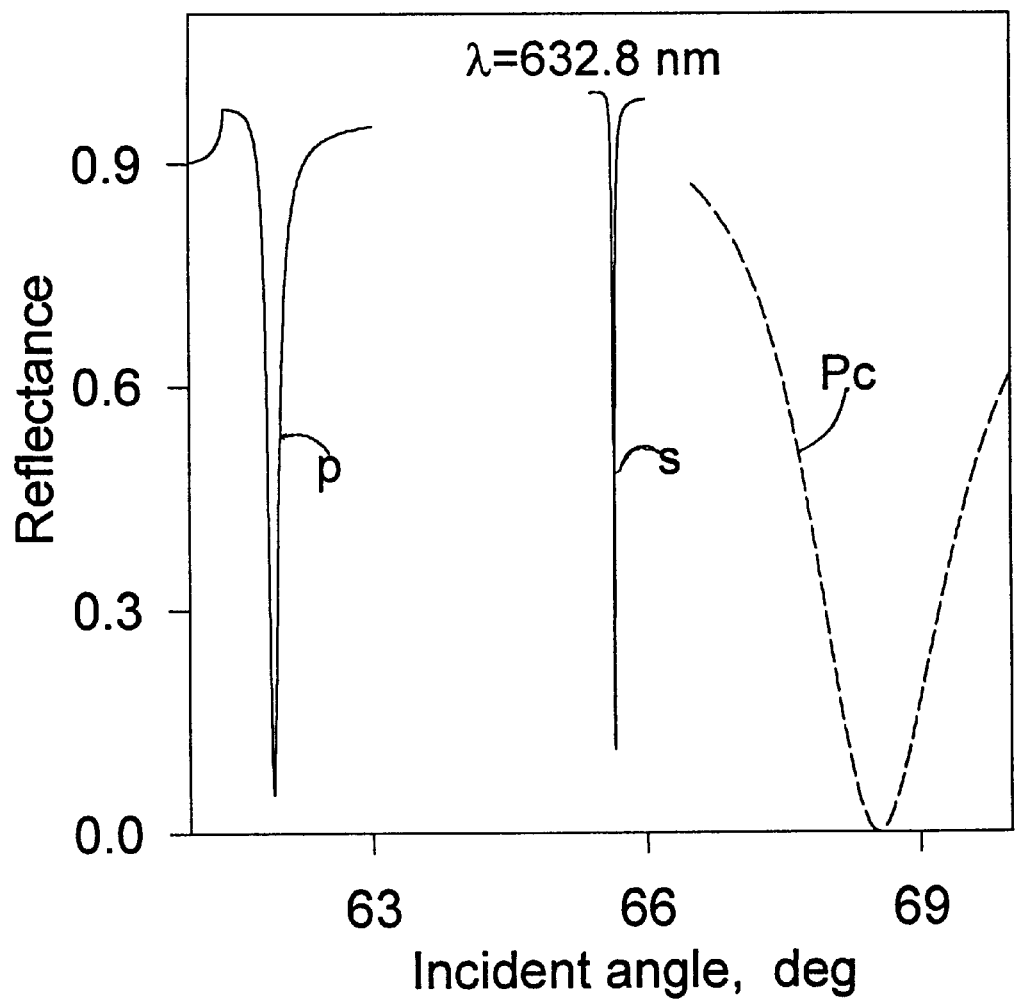
FIG. 7 shows resonance spectra obtained with the device of FIG. 3 presented as reflected light intensity versus incident angles.
Figure 8:
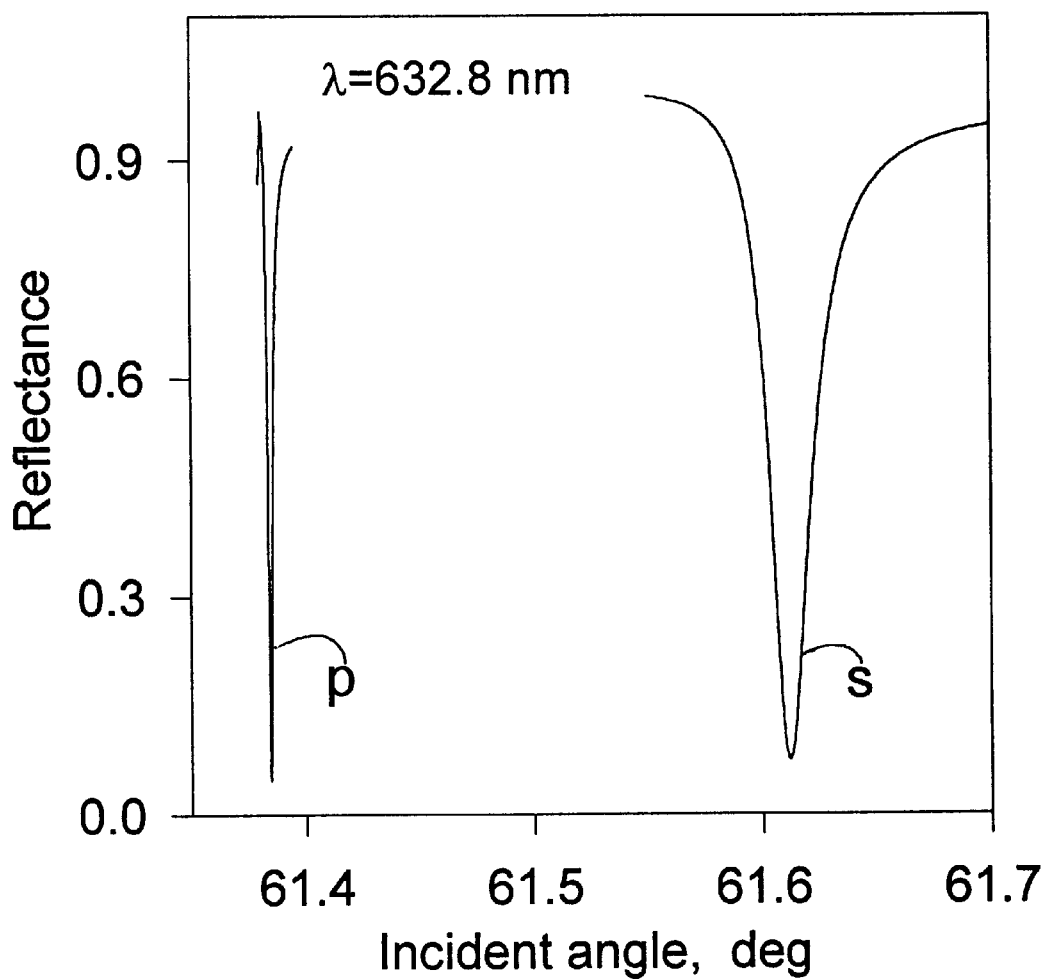
FIG. 8 shows resonance spectra obtained with the device of FIG. 4 presented as reflected light intensity versus incident angles.

FIG. 7 illustrates surface resonances measured as reflected light intensity as a function of the incident angle α with the apparatus 30 of FIG. 3, wherein reference symbols p and s identify curves generated with p- and s-polarized light, respectively. The dashed curve $p_c$ shows the much broader SPR spectrum obtained with the same silver layer of the device in FIG. 3 but with a conventional setup without the dielectric overcoat 32. FIG. 8 illustrates similar results obtained with the apparatus 40 of FIG. 4. These spectra show that the dielectric layer or layers add two very important features to conventional SPR resonance devices and procedures. The first is the additional spectroscopic dimension provided by generating a second type of resonance with different polarization (the s-polarized component). The second is the increased sensitivity resulting from the greatly decreased half-width of both s- and p-polarized resonances (as clearly seen in FIG. 7). Furthermore, the resonance half-width, and therefore the spectral sensitivity of the apparatus, can be adjusted by judiciously selecting appropriate overcoating layers and polarization mode of operation to meet specific experimental needs, as illustrated by the two sets of results shown in FIGS. 7 and 8. For example, these spectra show that the two dielectric layer designs of FIGS. 3 and 4 produced opposite spectral sensitivity. The device 30 yielded an s-spectrum narrower than the p-spectrum, whereas the opposite was true for the design of the device 40.

Figure 9:
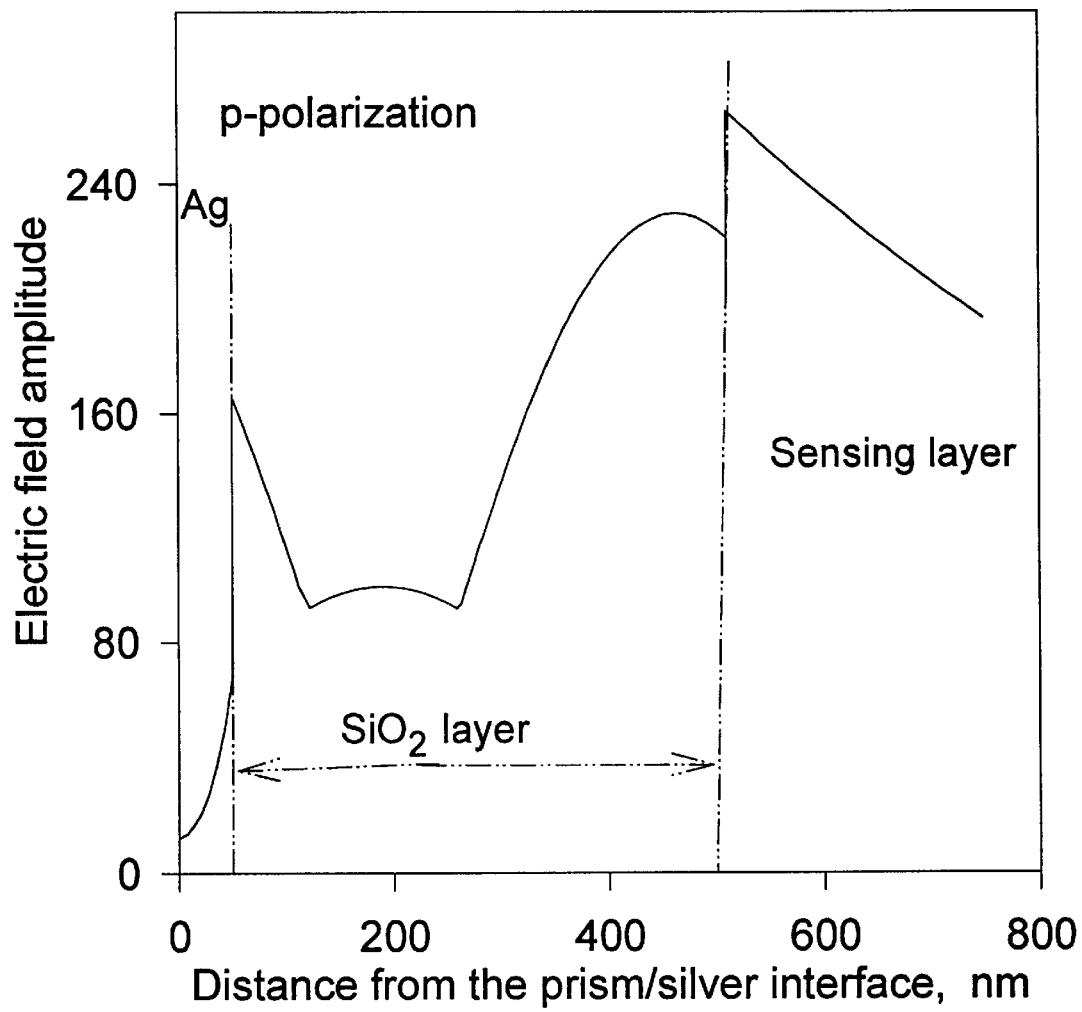
FIG. 9 shows the amplitude of the electric fields within a silver layer, an $SiO_2$ film, and a sensing layer for p-polarized light as a function of the distance from the glass-metal interface for the device shown in FIG. 3.
Figure 10:
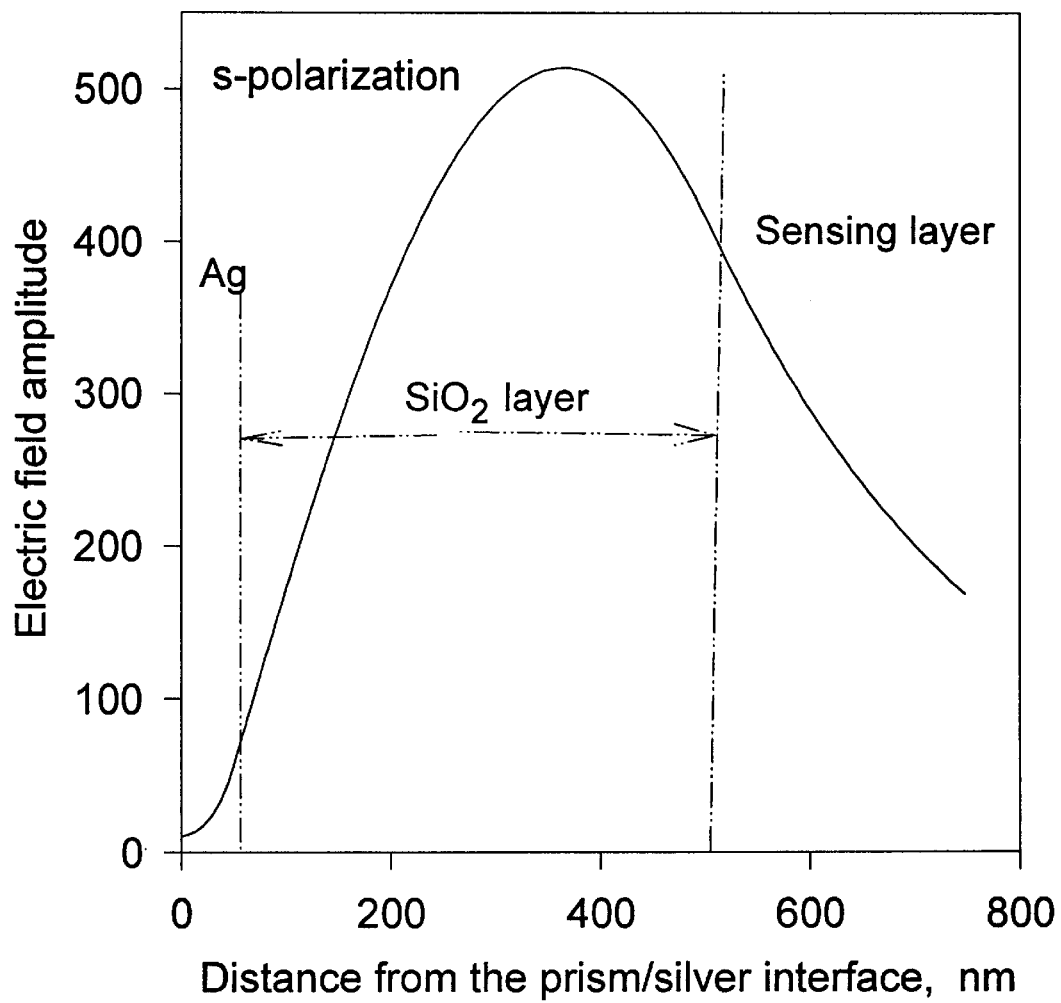
FIG. 10 shows the amplitude of the electric fields within a silver layer, an $SiO_2$ film, and a sensing layer for s-polarized light as a function of the distance from the glass-metal interface for the design shown in FIG. 3.

The overall sensitivity of the devices of the invention includes the sensitivity of the shift of the minimum resonance angle, which is determined in principle by the refractive index and thickness of the sensing layer 34 (for example a lipid bilayer deposited on the surface of the dielectric overcoat 32, as shown in FIG. 3). It also includes the sensitivity to the change in the shape of the resonance spectrum, which depends mainly on the light absorption (and/or scattering) properties of the sensing layer 32. Both of these parameters, i.e., the minimum resonance angle and the shape of the spectrum as defined by its depth and width, are dependent upon the form of the quasi-modes of the electromagnetic field generated in the combination of layers designed according to the invention. FIGS. 9 and 10 show the electric field distributions for p- and s-polarizations, respectively, obtained with the interface of the device 30 of FIG. 3. The figures show that the electric field at the outer interface between the dielectric 32 and the sensing layer 34 is higher by a factor of about 50 for the s-component, and about 25 for the p-component, in comparison with that at the entrance interface between the glass 16 and the metal layer 12. As a result of these properties and the corresponding higher sensitivity of the devices of the present invention, the three parameters that determine the resonance spectrum (thickness $t_e$, refractive index $n_e$, and extinction coefficient $k_e$ of the sensing layer 34) can be obtained with accuracies better than 1 Å, 0.001, and 0.002, respectively, for a sensing layer whose thickness is only 5 nm, a value comparable with the thickness of a lipid membrane (see Salamon, Z., Y. Wang, J. L. Soulages, M. F. Brown, and G. Tollin, "Surface Plasmon Resonance Spectroscopy Studies of Membrane Proteins: Transducin Binding and Activation by Rhodopsin Monitored in Thin Membrane Films," *Biophys. J.*, 71: 283–294, 1996; Salamon, Z. and G. Tollin, "Surface Plasmon Resonance Studies of Complex Formation Between Cytochrome c and Bovine Cytochrome c Oxidase Incorporated into a Supported Planar Lipid Bilayer. I: Binding of Cytochrome c to Cardiolipin/Phosphatidylcholine Membranes in the Absence of Oxidase," *Biophys. J.*, 11:848–857, 1996; and Salamon, Z. and G. Tollin, "Surface Plasmon Resonance Studies of Complex Formation Between Cytochrome c and Bovine Cytochrome c Oxidase Incorporated into a Supported Lipid Bilayer. II: Binding of Cytochrome c to Oxidase-Containing Cardiolipin/phosphatidylcholine Membranes," *Biophys. J.* 71: 858–867, 1996). In practical terms, this means that in many cases the limitation of accuracy in the procedure will result not from the measuring technique itself but from the ability to generate a thin sensing film in a reproducible manner.

Because of its characteristics, the present invention provides significant advantages over alternative techniques for the detection and measurement of small optical changes based on optical waveguides. The coupling arrangements are simple and convenient. Moreover, the geometric arrangement in CPWR spectroscopy is characterized by a complete isolation of the optical probe from the system under investigation, as is also the case in conventional SPR spectroscopy.

The three optical parameters ($n_d$, $k_d$, $t_d$) characterizing a deposited dielectric film 32 (or combination of films 32,38) can be evaluated for both polarizations, at different angles of light incidence, and using different light wavelengths. With these experimental data on hand, it is possible to characterize all of the structural parameters of thin films 34 under investigation, i.e., thickness, mass distribution within the film, orientation of molecules (by measuring the anisotropy in $n_e$), and the orientation of chromophores attached to the molecules within the sensing layer (by measuring the anisotropy of $k_e$). All of these characterizations can be obtained using a single device covered with a sensing layer 34, and using a measurement method that involves only a determination of reflected light intensity under total internal reflection conditions. Details of experimental techniques employed to measure the resonance spectrum are given in Salamon and Tollin (1996), supra, and Salamon et al. (1996), supra. Furthermore, because the electromagnetic field decays exponentially within the emerging medium (see FIGS. 9 and 10), the measurement is sensitive only to the interface region between the dielectric overcoat and the emerging medium, and is not affected by the bulk properties of the medium.

There is no limitation on the dielectric materials that can be used in the coatings 32,38 of the invention, as long as the optical characteristics are favorable, as explained above. Therefore, the dielectric film can be formed from any number of layers 32,38 designed and optimized for different uses. This feature is especially important in various sensor applications, where the dielectric overcoat can also be designed to adsorb and immobilize the sensing material either on its surface or within its interior. It is noted that the effects of the dielectric overcoat of the invention are not diminished by the addition of a very thin (1–5 nm) layer of gold or other metal at the interface with the emerging medium for the purpose of fixating the analyte to the sensing device, as already done with conventional SPR devices. Such a combination of properties in one interface permits the construction of a durable sensor device with very high sensitivity and an expanded dynamic range of measurements.

Although the features of the resonance spectrum produced by the present invention can be employed in a variety of different ways, one of the most fruitful applications lies in biophysical and biochemical studies of the structural properties of proteolipid assemblies. Studies of the microscopic structure of lipid membranes and interacting lipid-protein films represents a technically difficult challenge because they consist of very thin layers comprising only one or two monolayers. In addition, they contain relatively small amounts of material located at the interface between two immiscible phases, and may be labile and structurally heterogeneous. As a result, only a limited number of studies have been made of lipid and/or protein orientation in molecular films. The following example demonstrated the suitability and improved capabilities of the invention in obtaining information about structural anisotropy in a self-assembled solid-supported lipid bilayer.

EXAMPLE

Self-assembled solid supported lipid membranes were used as described by Salamon et al. (1996), supra, to illustrate the features of the invention. The method of preparation of lipid membranes was based on the principles that govern the spontaneous formation of a freely suspended lipid bilayer membrane, as described in Mueller, P., D. O. Rudin, H. T. Tien and W. C. Wescott, "Reconstitution of Cell Membrane Structure in vitro and its Transformation into an Excitable System," Nature, 194: 979–980, 1962. As illustrated in the device 30 of FIG. 3, the method involves spreading a small amount of lipid bilayer-forming solution 20 (about 24 μL) across an orifice (about 4 mm in diameter) in a TEFLON® sheet (the spacer 36) that separates the dielectric thin film 32 of the invention from the aqueous phase 20 (for further detail, see Salamon et al., 1997, supra). The hydrophilic surface of the dielectric layer 32 (hydrated $SiO_2$ in the present case) attracts the polar groups of the lipid molecules, thus forming an adsorbed lipid monolayer with the hydrocarbon chains oriented toward the bulk lipid phase. Subsequent to the first step of lipid membrane formation, the main body of the sample cell is filled with the appropriate aqueous solution. This initiates the second step, which involves a thinning process, i.e., the formation of both the second monolayer and a plateau-Gibbs border that anchors the bilayer film 34 to the TEFLON® spacer 36, allowing the excess of lipid and solvent to move out of the TEFLON® orifice. Previous work involving both SPR and electrochemical measurements with different protein molecules demonstrated that this technique generates a membrane that provides a biocompatible medium for binding and immobilizing both peripheral and integral membrane proteins. See Salamon, Z., J. T. Hazzard and G. Tollin, "Direct Measurement of Cyclic Current-Voltage Responses of Integral Membrane Proteins at a Self-Assembled Lipid Bilayer-Modified Electrode: Cytochrome f and Cytochrome c Oxidase," Proc. Natl. Acad. Sci. USA, 90: 6420–6423 (1993); Salamon, Z., Y. Wang et al. (1996), supra; and Salamon and Tollin (1996), supra. In the experiment of this example, the lipid films were formed on the $SiO_2$ surface from solutions containing 7 mg/mL of egg phosphatidylcholine (PC) in squalene (Fluka)/butanol (0.15:10, v/v), using thin film coatings prepared at the Tucson Optical Research Co. in Tucson, Ariz., by vacuum deposition. The egg PC was obtained in solid form from Avanti Polar Lipids (Alabaster, Ala.).

Figure 11:
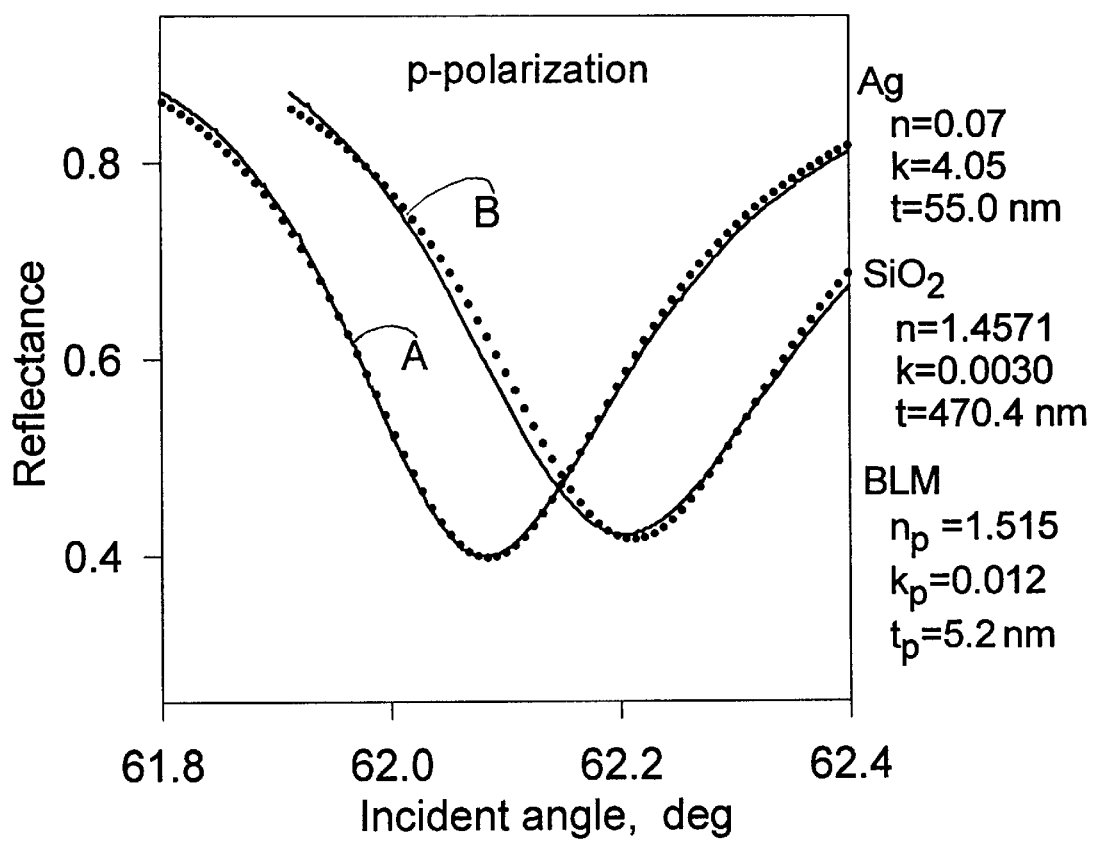
FIG. 11 shows experimental resonances (points) and theoretical fits (lines) obtained with the device illustrated in FIG. 3 with p-polarized light before and after depositing an egg phosphatidylcholine bilayer onto the $SiO_2$ surface.
Figure 12:
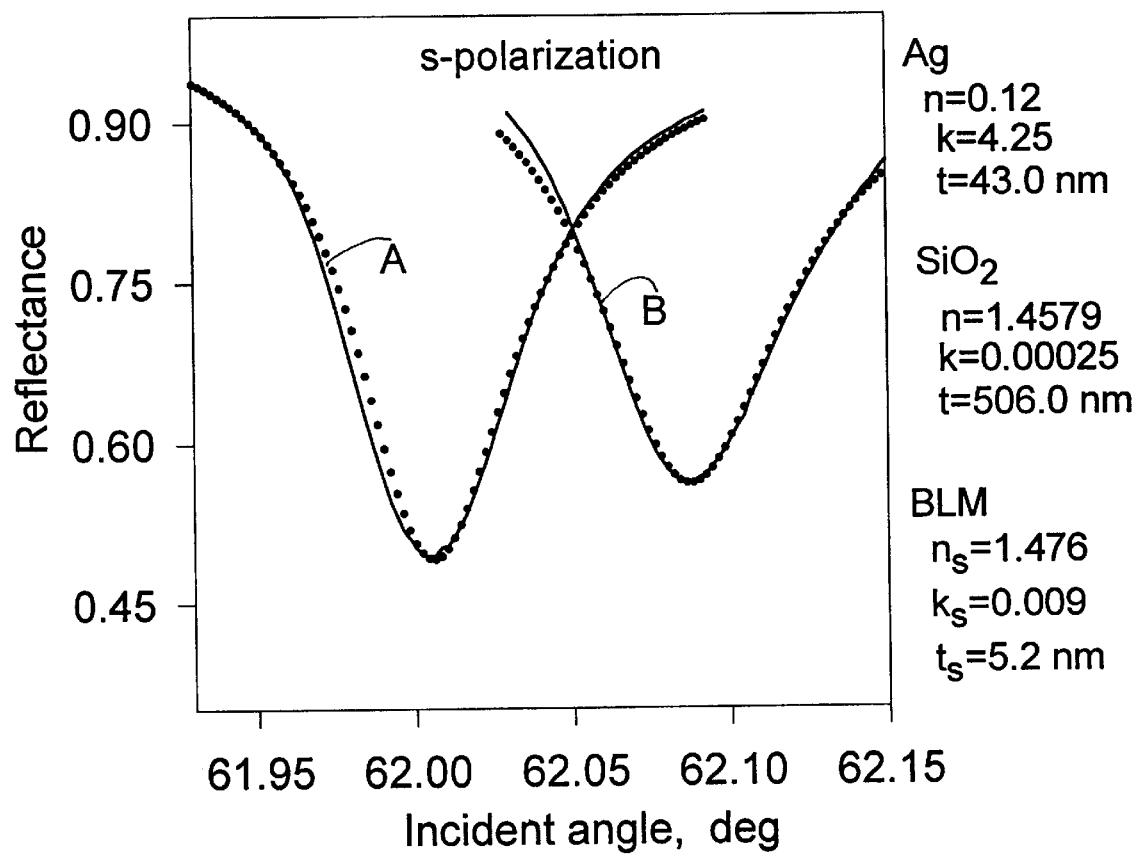
FIG. 12 shows experimental resonances (points) and theoretical fits (lines) obtained with the same device used for FIG. 11 with s-polarized light before and after depositing an egg phosphatidylcholine bilayer onto the $SiO_2$ surface.

In general, the experimental procedures for resonance spectra measurement and data analysis for the CPWR devices of the invention are the same as with conventional SPR studies and are well described in the literature (see Salamon and Tollin, 1997, supra; and Salamon et al., 1997, supra). The measurements for this example were performed in two different ways. First, the resonance spectra generated by both s- and p-polarization were measured with the device 30 of FIG. 3 with a single lipid membrane. Then, the two different devices in the configuration of FIG. 3 (with varying metal and dielectric coating layer parameters, as shown in the figures) with two separately formed lipid bilayers 34 were used in measuring the resonance spectrum generated by each polarization. This was done in order to evaluate the experimental errors produced by the formation of new lipid membranes and by using different thin film coatings. FIG. 11 shows a typical example of the resonance spectra obtained with the second procedure and p-polarized light, using a bare $SiO_2$ film 32 (curve A) and modified by depositing an egg PC bilayer membrane (curve B). FIG. 12 shows the results of the same measurements generated by s-polarization.

Calculations of the electric fields throughout the thin-film system consisting of the CWPR device and the deposited lipid bilayer show that for p-polarized light the amplitude of the component of the electric field normal to the film boundaries is an order of magnitude larger than that parallel to the surface (as illustrated in FIGS. 9 and 10). In s-polarized excitation the field is completely parallel to the boundaries. Therefore, a good first approximation is to assume that in the p-polarization case the electric vector is completely normal to the surface. As a consequence, the optical parameters obtained with these two modes of excitation refer to the parallel and perpendicular directions within the lipid film.

Table 1 below shows average values of thickness, refractive index, and extinction coefficient of a self-assembled solid-supported egg phosphatidylcholine bilayer obtained by measuring CPWR resonance spectra excited either by p- or s-polarized light in this example. The table also shows the experimental errors resulting from the different measurement procedures described above. These results clearly indicate that, although the thickness values obtained with both polarizations are the same within the experimental error, and compare well with those obtained previously with conventional SPR techniques (see Salamon et al., 1996, supra), there are significant differences in both the n and k parameter values.

TABLE 1

| parameter | p | s |
|---|---|---|
| t (nm) | 5.2 ± 0.1 | 5.2 ± 0.1 |
| n | 1.52 ± 0.01 | 1.47 ± 0.01 |
| k | 0.10 ± 0.01 | 0.020 ± 0.002 |

In this type of measurement, the anisotropy in n may derive from the two-dimensional nature of the film 34 and from the ordering of anisotropic molecules within the two-dimensional structure. Simple calculations show that the difference in the index of refraction between the n- and p-polarization results is too large to be explained by a form birefringence. Thus, the source of the anisotropy in n must be the anisotropic character of the lipid molecules comprising the bilayer structure. Because in this experiment the lipid did not absorb the exciting light (the wavelength of the laser excitation, 632.8 nm, is far from the absorption band of PC), a k value different than zero reflects a diminution of measured light intensity due only to scattering processes which result from imperfections in the lipid film. It is expected that in anisotropic films the two polarized components of light will be scattered differently, thereby producing a scattering anisotropy.

The value obtained for the refractive index with p-polarization agrees rather well with those obtained by previous measurements using SPR with a bare silver layer (Salamon et al., 1996, supra). Although with a complex mixture such as egg PC it was not possible to calculate theoretical polarizabilities and refractive indices for comparison, the average experimental values of refractive index shown in Table 1 are in very good agreement with theoretical values of these indices calculated for five different lipid molecules containing saturated fatty acid side chains (the average values are: n=1.559 with p-polarization; and n=1.483 with s-polarization), assuming the additivity principle in tetrahedral aliphatic hydrocarbons (see Den Engelsen, "Optical Anisotropy in Ordered Systems of Lipids," *Surf. Sci.*, 56: 272–280, 1976) and assuming ellipsometrically measured values of various phospatidylcholines (see Ducharme, D., J. Max, C. Saleese and R. M. Leblanc, "Ellipsometric Study of the Physical States of Phosphatidylcholines at the Air-Water Interface," *J. Phys. Chem.*, 94: 1925–1932, 1990). This similarity clearly indicates a high degree of ordering of the egg PC molecules in the solid-supported self-assembled lipid bilayer system used in the example. The refractive index anisotropy obtained in these measurements seems to be larger than that calculated from ellipsometric determinations on freely suspended black lipid membranes of lecithin, where values of n=1.47 and n=1.45 (for p- and s-polarizaton, respectively) have been reported in the literature (Den Engelsen, 1976, supra). This indicates a higher degree of ordering of the PC molecules in the solid-supported membrane, which is not unexpected.

These results clearly demonstrate that CPWR spectroscopy provides a useful new technique for obtaining information about molecular assemblies which can be immobilized at a dielectric/water interface. Three major improvements over conventional SPR methodologies have been documented: increased spectral resolution, improved sensitivity, and the ability to measure anisotropy in both n and k. Furthermore, the method is applicable to a wide range of materials, including, without limitation, lipid membranes that have either integral membrane proteins incorporated into them or peripheral membrane proteins bound to their surface.

Various changes in the details, steps and components that have been described may be made by those skilled in the art within the principles and scope of the invention herein illustrated and defined in the appended claims. For example, other dielectric materials with n and k parameters suitable for the invention could be used. For a given material and other system parameters, a range of thicknesses could be used with equivalent results. For example, the system of FIG. 3 can be implemented with any $SiO_2$ layer greater than 420 nm; the same system can be implemented with any $TiO_2$ layer greater than 750 nm. Similarly, the observable range can be increased or decreased by changing the properties of the prism and/or the emerging medium. For example, changing the prism to a material with n=2.2 would essentially double the observable range from about 61–90 degrees to 35–90 degrees in a system with an aqueous emerging medium.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and devices.

I claim:

1. In a surface-plasmon-resonance spectroscopic device, wherein a surface plasmon is excited by a light beam and propagated along a metallic or semiconductor film to measure a property of a sample material placed at an interface of an emergent medium, the improvement comprising a dielectric member inserted between said film and said emergent medium, wherein said dielectric member is selected such that resonance effects are produced within an observable range, and wherein said dielectric member comprises a dielectric material selected from the group consisting of $SiO_2$, $TiO_2$, $MgF_2$, $Al_2O_3$, $LaF_3$, $Na_3AlF_6$, $ZnS$, $ZiO_2$, $Y_2O_3$, $HfO_3$, $Ta_2O_5$, ITO, and nitrites or oxy-nitrites of silicon and aluminum, and mixtures thereof.

2. The device of claim 1, wherein said dielectric member consists of a single layer of dielectric material.

3. The device of claim 1, wherein said film consists substantially of silver or gold.

4. The device of claim 1, wherein said sample material comprises a lipid layer.

5. The device of claim 1, wherein said film consists substantially of silver or gold and said sample material comprises a lipid layer.

6. The device of claim 2, wherein said single layer of dielectric material is selected from the group consisting of $SiO_2$, $TiO_2$, $MgF_2$, $Al_2O_3$, $LaF_3$, $Na_3AlF_6$, $ZnS$, $ZiO_2$, $Y_2O_3$, HfO$_3$, Ta$_2$O$_5$, ITO, and nitrites or oxy-nitrites of silicon and aluminum, and mixtures thereof.

7. The device of claim 1, wherein said single layer is SiO$_2$ at least 420 nm thick.

8. The device of claim 1, wherein said single layer is TiO$_2$ at least 750 nm thick.

9. The device of claim 1, wherein said dielectric member comprises a first layer of dielectric material having a predetermined density and a second layer of dielectric material having a lower density; the first layer being in contact with said film and the second layer being in contact with said sample material.

10. The device of claim 9, wherein said first layer of dielectric material is selected from said group consisting of SiO$_2$, TiO$_2$, MgF$_2$, Al$_2$O$_3$, LaF$_3$, Na$_3$AlF$_6$, ZnS, ZiO$_2$, Y$_2$O$_3$, HfO$_3$, Ta$_2$O$_5$, ITO, and nitrites or oxy-nitrites of silicon and aluminum, and mixtures thereof.

11. The device of claim 9, wherein said second layer is a hydrogel material.

12. The device of claim 9, wherein said first layer is SiO$_2$ at least 420 nm thick.

13. The device of claim 9, wherein said second layer is TiO$_2$ at least 750 nm thick.

14. The device of claim 9, wherein said film consists substantially of silver or gold.

15. The device of claim 9, wherein said sample material comprises a lipid layer.

16. A method for measuring a property of a sample material present at an interface of an emerging medium in a surface-plasmon-resonance spectroscopic device, wherein a surface plasmon is excited by a light beam and propagated along a metallic or semiconductor film, comprising the following steps:

(a) coating said film with a dielectric member;

(b) placing said dielectric member at said interface of the emerging medium of the surface-plasmon-resonance spectroscopic device; and (c) performing surface-plasmon-resonance spectroscopic measurements according to conventional procedures;

wherein said dielectric member comprises a first layer of dielectric material having a predetermined density and a second layer of dielectric material comprising a lower-density matrix; the first layer being in contact with said film and the second layer being in contact with said sample material.

17. The method of claim 16, wherein said sample material comprises a lipid layer adsorbed and immobilizing into said matrix of the second layer of dielectric material.

18. The method of claim 16, wherein said light beam is either s- or p-polarized.

19. In a conventional surface-plasmon-resonance spectroscopic device, wherein a surface plasmon is excited by a light beam and propagated along a metallic or semiconductor film to measure a property of a sample material placed at an interface of an emergent medium, the improvement comprising a dielectric member inserted between said film and said emergent medium, wherein said metallic or semiconductor film is selected in a thickness sufficient to prevent excitation of surface-bound waves on both sides thereof, and wherein said dielectric member is selected such that coupled plasmon-waveguide resonance effects are produced within an observable range.

20. A method for measuring a property of a sample material present at an interface of an emerging medium in a surface-plasmon-resonance spectroscopic device, wherein a surface plasmon is excited by a light beam and propagated along a metallic or semiconductor film sufficiently thick to prevent excitation of surface-bound waves on both sides thereof, comprising the following steps:

(a) coating said film with a dielectric member selected such that coupled plasmon-waveguide resonance effects are produced within an observable range;

(b) placing said dielectric member at said interface of the emerging medium of the surface-plasmon-resonance spectroscopic device; and (c) performing surface-plasmon-resonance spectroscopic measurements according to conventional procedures.

* * * * *